US00PP19408P3

(12) United States Plant Patent
Hambali

(10) Patent No.: US PP19,408 P3
(45) Date of Patent: Nov. 4, 2008

(54) ***AGLAONEMA* PLANT NAMED 'TWYAG0057'**

(50) Latin Name: ***Aglaonema* hybrid**
Varietal Denomination: TWYAG0057

(75) Inventor: Gregori Garnadi Hambali, Bogor (ID)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 0 days.

(21) Appl. No.: 11/654,763

(22) Filed: Jan. 18, 2007

(65) Prior Publication Data

US 2008/0184427 P1 Jul. 31, 2008

(51) Int. Cl.
*A01H 5/00* (2006.01)

(52) U.S. Cl. ..... Plt./376

(58) Field of Classification Search ..... Plt./376
See application file for complete search history.

*Primary Examiner*—Annette H Para
*Assistant Examiner*—S. B. McCormick-Ewoldt
(74) *Attorney, Agent, or Firm*—Jondle & Associates, P.C.

(57) ABSTRACT

A new *Aglaonema* plant particularly distinguished by having a dense, full, upright, moderately branched growth habit and consistent progressive growth and being intermediate in stature is disclosed.

1 Drawing Sheet

Genus and species: *Aglaonema* hybrid.
Variety denomination: 'TWYAG0057'.

BACKGROUND OF THE NEW PLANT

The present invention comprises a new and distinct cultivar of *Aglaonema,* botanically known as *Aglaonema* hybrid, and hereinafter referred to by the cultivar name 'TWYAG0057'. The new cultivar originated as a naturally-occurring branch mutation of an individual plant of *Aglaonema* 'Donna Carmen' (unpatented) in 2002. 'TWYAG0057' was first propagated by cuttings and sucker division in January, 2003 in W. Java, Indonesia and then by cuttings and tissue culture in Apopka, Fla.

The new cultivar was created in W. Java, Indonesia and has been asexually reproduced repeatedly by vegetative cuttings and tissue culture in Apopka, Fla. The present invention has been found to retain its distinctive characteristics through successive asexual propagations.

SUMMARY OF THE INVENTION

The following are the most outstanding and distinguishing characteristics of this new cultivar when grown under normal horticultural practices in Apopka, Fla.

1. Intermediate in stature;
2. Dense, full, upright, moderately branched growth habit; and
3. Consistent progressive growth.

DESCRIPTION OF PHOTOGRAPH

This new *Aglaonema* plant is illustrated by the accompanying photograph which shows the upper and lower surface of a mature leaf of the plant. The colors shown are as true as can be reasonably obtained by conventional photographic procedures.

DESCRIPTION OF THE NEW CULTIVAR

The following detailed description sets forth the distinctive characteristics of 'TWYAG0057'. The data which define these characteristics were collected from asexual reproductions carried out in Apopka. Fla. The plant history was taken on 16-month old plants started from a single 4-leaf rooted cutting, still in a vegetative state and grown in Apopka, Fla. Rooted cuttings were planted in 20-cm pots and grown in a greenhouse in May 2006. The plants were pinched twice. Color readings were taken under natural light. Color references are primarily to the R.H.S. Colour Chart of The Royal Horticultural Society of London (R.H.S.) (2001).

DETAILED BOTANICAL DESCRIPTION

Classification:
- *Family.*—Araceae.
- *Botanical.*—*Aglaonema* hybrid.
- *Common name.*—Chinese Evergreen.

Parentage: Branch mutation of *Aglaonema* 'Donna Carmen'.

Growth:
- *Form.*—Symmetrical, upright, wider than tall.
- *Growth and branching habit.*—Dense, full, upright, moderately branched growth habit (basal branching); intermediate in stature.
- *Height (from soil to top of leaf plane).*—27 cm to 31 cm.
- *Diameter (area of spread, measured from leaf tip to leaf tip across the canopy).*—55 cm to 58 cm.
- *Time to produce a finished flowering plant.*—16-months starting from a single 4-leaf rooted cutting and pinched twice.
- *Root description.*—Abundant, fleshy roots white than but closest to RHS 155C, with finer lateral branches.
- *Number of divisions or clumps per year.*—About 5 to 8 4-leaf cuttings per year.
- *Durability of foliage to stresses.*—Leaves hold up well against damage from shipping and handling; plant is durable, excellent indoor keeping quality.

*High temperature tolerance.*—To about 104° F. for several hours without Damage.

*Low temperature tolerance.*—To about 55° F. for several hours without damage.

Stems:

*Number of branches per plant.*—12.

*Length (from soil line to the junction of the newest two leaves).*—14 cm.

*Diameter.*—1.3 cm.

*Internode length.*—0.9 cm to 2.2 cm.

*Color.*—Immature: RHS 146C to RHS 146D mottled with a color between RHS 146A and RHS 147A. Mature: RHS 147A and RHS 146A mottled with a color between RHS 165D and RHS 158A. Oldest stems: RHS 147A marbled with RHS 158A to RHS 158B.

*Appearance (shape).*—Columnar, cylindrical upright.

*Aspect.*—Vertical, upright.

*Strength.*—Sturdy, strong, somewhat flexible.

*Axillary buds.*—Shape: Elliptic, flat. Length: 0.6 cm. Width: 0.35 cm. Color: RHS 145D tinged with RHS 158A.

Leaves:

*Arrangement.*—Alternate, single, arranged in a spiral along the stem.

*Quantity of leaves per stem.*—7.

*Quantity of leaflets per leaf.*—Single, simple.

*Young leaf (New expanded leaf).*—Color: Upper side: Base color darker and greener than, but closest to RHS 147A with random spots of RHS N170D and RHS 49B to RHS 49C. Under side: Base color darker and greener than, but closest to RHS 147A to RHS 147B with random spots of RHS N170D and RHS 49B to RHS 49C.

*Mature leaf.*—Color: Upper side: Base color much darker and greener than, but closest to a color between RHS 147A and RHS 139A with random spots of RHS 49C to RHS 49D, RHS 49B to RHS 49C, and RHS 145D. Under side: Base color between RHS 147B and RHS 146A with random spots of RHS 49C to RHS 49D and RHS 49B to RHS 49C.

*Length.*—14.5 cm to 16.0 cm.

*Width.*—Flattened: 7.5 cm to 10.0 cm. Not flattened (natural width): 6.5 cm to 8.0 cm.

*Shape.*—Elliptic.

*Apex.*—Tips often bluntly rounded, cuspidate to obtuse; distal portion often cupped upward.

*Base.*—Obtuse.

*Margin.*—Smooth, entire, mostly flat with some broad undulations.

*Texture.*—Smooth, stiff, leathery; new leaves shiny to glossy; mature leaves glossy; the leaf blade is flat between the main veins or slightly puckered along the midrib.

*Pubescence.*—None.

*Venation pattern.*—Pinnate, radiating outward from the midrib in a herringbone arrangement.

*Venation color (Newly expanded leaf).*—Upper side: Primary veins: RHS 150D. Midrib: RHS 48D. Under side: Primary veins: RHS 155C tinged with RHS 69C. Midrib-proximal: Between RHS 147B and RHS 146A with tiny spots of RHS 146D. Midrib-distal: RHS 49B.

*Venation color (Mature leaf).*—Upper side: Primary veins: RHS 147C to RHS 147D. Midrib: RHS 63C often darkening with age to RHS 58A. Under side: Primary veins: RHS 155C. Midrib-proximal: Between RHS 147B and RHS 146B with tiny spots of RHS 146D. Midrib-distal: RHS 49C to RHS 49D.

*Petioles.*—Aspect: Vertical upright when newly expanded, becoming curved outward and about 45° with maturity. Length: 8.0 cm to 14 cm. Diameter: Distal: 0.45 cm. Proximal (petiole and petiole sheath clasps the stem proximally): Flattened: 2.3 cm. Natural diameter: 1.3 cm with a depth of 0.6. Color: Distal: RHS 147A with fine spots of RHS 147D (between the top of the wing and the base of the leaf). Proximal: RHS 147A to RHS 147B with fine spots and streaks of RHS 147D. Area adjacent to stem: RHS 146D tinged with RHS 160D. Wing length: 5.9 cm. Wing diameter: Mid-point: 1.0 cm. Base: 1.3 cm. Depth: 0.6 cm. Wing color: Variably marked with RHS 155C often tinged with RHS 49D. Inside: RHS N155C tinged with RHS 146C on sides. Outside: RHS 147A to RHS 147B with fine spots and streaks of RHS 147D.

Fruit and seed set: None observed.

Disease and insect resistance: No special observations made.

COMPARISON WITH PARENTAL AND COMMERCIAL CULTIVARS

'TWYAG0057' differs from its mutation parent 'Donna Carmen' (unpatented) in that 'TWYAG0057' has dark green leaves while 'Donna Carmen' has pale green leaves with a pinkish tint.

'TWYAG0057' differs from the commercial cultivar 'Pride of Sumatra' (unpatented) in that 'TWYAG0057' lacks inflorescences while 'Pride of Sumatra' has inflorescences. In addition, the leaves of 'TWYAG0057' have spots and dark green undersides at maturity while the leaves of 'Pride of Sumatra' lack spots and have maroon undersides at maturity.

'TWYAG0057' differs from the commercial cultivar 'WYAG0003' (U.S. Plant Pat. No. 17,673) in that 'TWYAG0057' has a taller more upright growth habit than 'TWYAG0003'. In addition, 'TWYAG0057' has leaves with a prominent pink midrib while 'TWYAG0003' has leaves lacking a prominent pink midrib.

I claim:

1. A new and distinct cultivar of *Aglaonema* plant as shown and described herein.

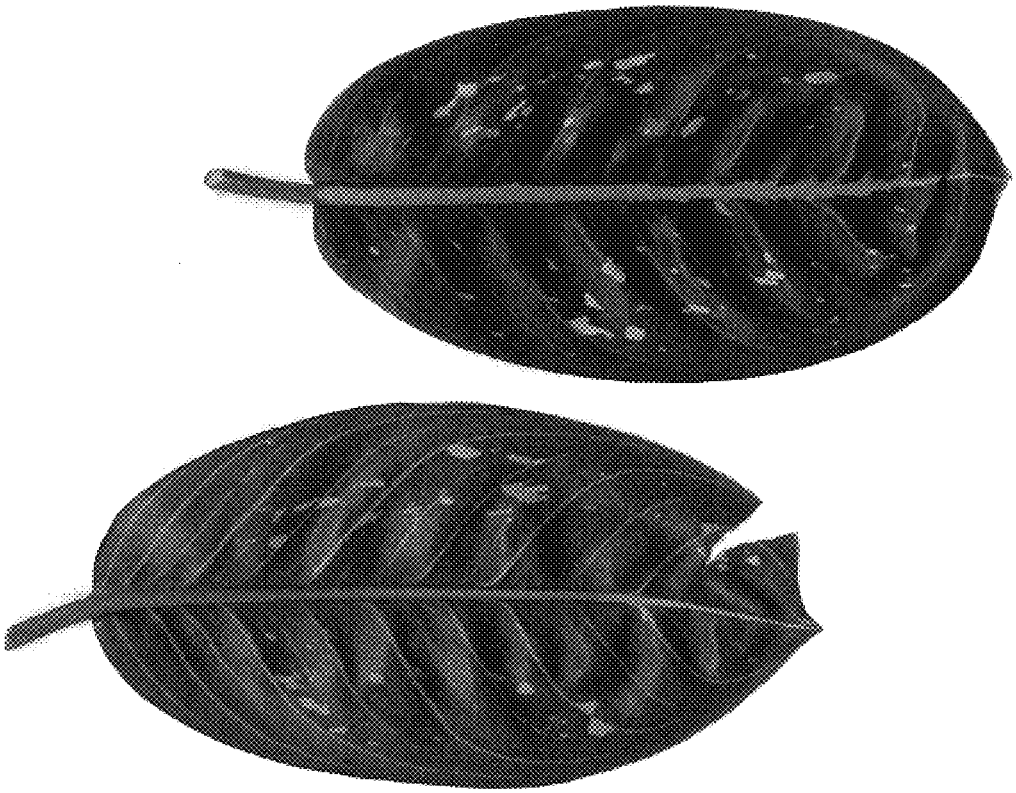

* * * * *